US00PP25589P3

(12) United States Plant Patent
Fang

(10) Patent No.: US PP25,589 P3
(45) Date of Patent: May 26, 2015

(54) ***ONCIDIUM* SWEET SUGAR 'LEMON DROP'**

(50) Latin Name: ***Oncidium* Sweet Sugar**
Varietal Denomination: Lemon Drop

(71) Applicant: James Yen Jen Fang, Mountain View, HI (US)

(72) Inventor: James Yen Jen Fang, Mountain View, HI (US)

( * ) Notice: Subject to any disclaimer, the term of this patent is extended or adjusted under 35 U.S.C. 154(b) by 193 days.

(21) Appl. No.: 13/694,938

(22) Filed: Jan. 23, 2013

(65) Prior Publication Data

US 2014/0208474 P1 Jul. 24, 2014

(51) Int. Cl.
*A01H 5/02* (2006.01)

(52) U.S. Cl.
CPC ..... *A01H 5/02* (2013.01)
USPC ..... Plt./311

(58) Field of Classification Search
CPC ..... A01H 5/02; A01H 5/00
USPC ..... Plt./311
See application file for complete search history.

*Primary Examiner* — Kent L Bell

(57) ABSTRACT

A new variety of orchid plant of the genus *Oncidium*, named *Oncidium* Sweet Sugar 'Lemon Drop', distinguished particularly by flowers of a clean and striking color of medium size that are arranged pleasingly on a raceme and growing quickly to sexual maturity.

2 Drawing Sheets

Latin name of the species and grex of the plant claimed: The Latin name of the Species and grex of the plant claimed is *Oncidium* Sweet Sugar.

Variety denomination: The present invention comprises a new and distinct cultivar of *Oncidium* orchid and hereinafter referred to by the name *Oncidium* Sweet Sugar 'Lemon Drop'.

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The genus *Oncidium* is one of the largest and most diverse within the orchid family; numbering more than 600 distinct species distributed throughout the American tropics and extending into South-Central America.

Many, if not most of the species within the genus, grow as epiphytes. The remaining species thrive growing as lithophytes or terrestrials. All exhibit a sympodial growth habit.

The first *Oncidium* hybrid was created in 1898 by a Mr. C. Vuylsteke and registered by the same.

*Oncidium* hybridizing is accomplished through sexual methods. Asexual propagation of *Oncidium* is done in aseptic tissue culture from apical or axillary shoots.

The new cultivar was discovered within a group of asexually produced plants on Aug. 10, 2008. The inventor selected *Oncidium* Sweet Sugar 'Lemon Drop' from a population of over 3000 plants grown in Mountain View, Hi. *Oncidium* Sweet Sugar 'Lemon Drop' was re-flowered on May 20, 2009 and submitted by the inventor to a commercial tissue culture laboratory in Bangkok, Thailand on Feb. 24, 2010 for propagation through aseptic tissue culture technique.

Other seedlings of the same varieties that were used to produce *Oncidium* Sweet Sugar 'Lemon Drop' have been commercially available from others. The characteristics of *Oncidium* Sweet Sugar 'Lemon Drop' as described herein have demonstrated to be fixed and retained through successive generations of asexual reproduction. *Oncidium* Sweet Sugar 'Lemon Drop' reproduces true to type. The characteristics are clearly distinguishable from the characteristics of those other plants. The inventor has reason to believe that *Oncidium* Sweet Sugar 'Lemon Drop' is superior to other seedlings in flower color.

BRIEF SUMMARY OF THE INVENTION

The following traits have been repeatedly observed and are determined to be basic characteristics of the new cultivar which in combination distinguish this *Oncidium* orchid as a new and distinct cultivar:

Flowers of the new cultivar are bright yellow in color with irregular crystalline light green striations on the sepals and petals. The labellum is bright yellow with a darker yellow center extending from the callus. The callus is matte yellow with white apical surfaces and develops as a swelling in the lip throat terminating into many small diverging horns divided by a central crest about 0.5 centimeters (cm) long. The anther cap is bright yellow in color. The column is of similar color, but overlaid light crystalline green. The column wings are rectangular and bright yellow in color. The flowers are rigid and bear no fragrance.

The natural horizontal spread is 4.5 cm; natural vertical spread is 5.4 cm; dorsal sepal width 0.5 cm; dorsal sepal length 1.2 cm; petal width 0.6 cm; petal length 1 cm; lateral sepal width 0.6 cm; lateral sepal length 1 cm; labellum width 4.5 cm; labellum length 4 cm.

The plant produces one branching inflorescence on first bloom with 35 flowers.

Inflorescence is a basal raceme, upright or arching, branching and approximately 60 cm long. The plant is relatively compact and the size of the inflorescence is appropriate to the overall size of the plant and typical pot size for this cultivar.

There are generally four leaves per mature psuedobulb: two from the apex and two from the base. The apical leaves measure 20 cm long and are 5 cm wide. The leaves from the base of the psuedobulb measure 6-12 cm long and are 4 cm wide. Axillary leaves, or bracts, are not common below the leaves at the base of the psuedobulb. The shape of the leaf is lanceolate acuminate and they are semi-conduplicate at the base. The texture and substance is slightly undulate and somewhat coriaceous. The plants of *Oncidium* Sweet Sugar 'Lemon Drop' grow to maturity and flower in approximately 16 months.

Plants of the new cultivar have not been observed under all possible environmental conditions. The phenotype may vary significantly with variations in the environment, such as temperature, light intensity, and day length, without any change in genotype.

Plants of the new cultivar differ primarily from the plants of the parent cultivars in flower color. Perhaps the closest commercial comparison to the new cultivar can be made to the plant material used in the aseptic tissue culture technique used to create *Oncidium* Sweet Sugar 'Lemon Drop'. The original unpatented plant material; named *Oncidium* Sweet Sugar 'Million Dollar' possesses the same growth habit and speed to maturation, but lacks the unique, attractively large yellow flowers of *Oncidium* Sweet Sugar 'Lemon Drop'.

BRIEF DESCRIPTION OF THE DRAWINGS

The drawings show the colors of the new variety as nearly true as possible with an illustration of this type. In the drawings:

The drawing on the first sheet is a single flower to illustrate shape.

Figure 1:
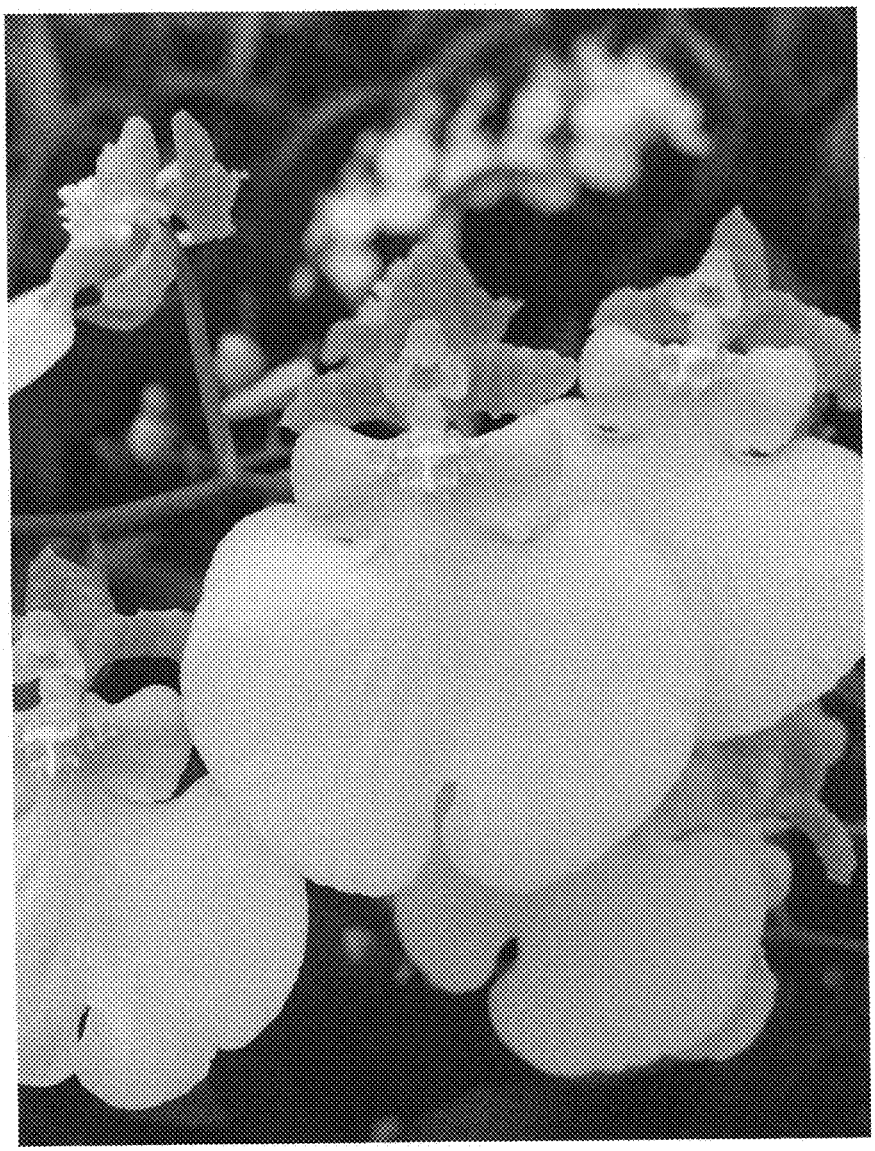
Figure 2:
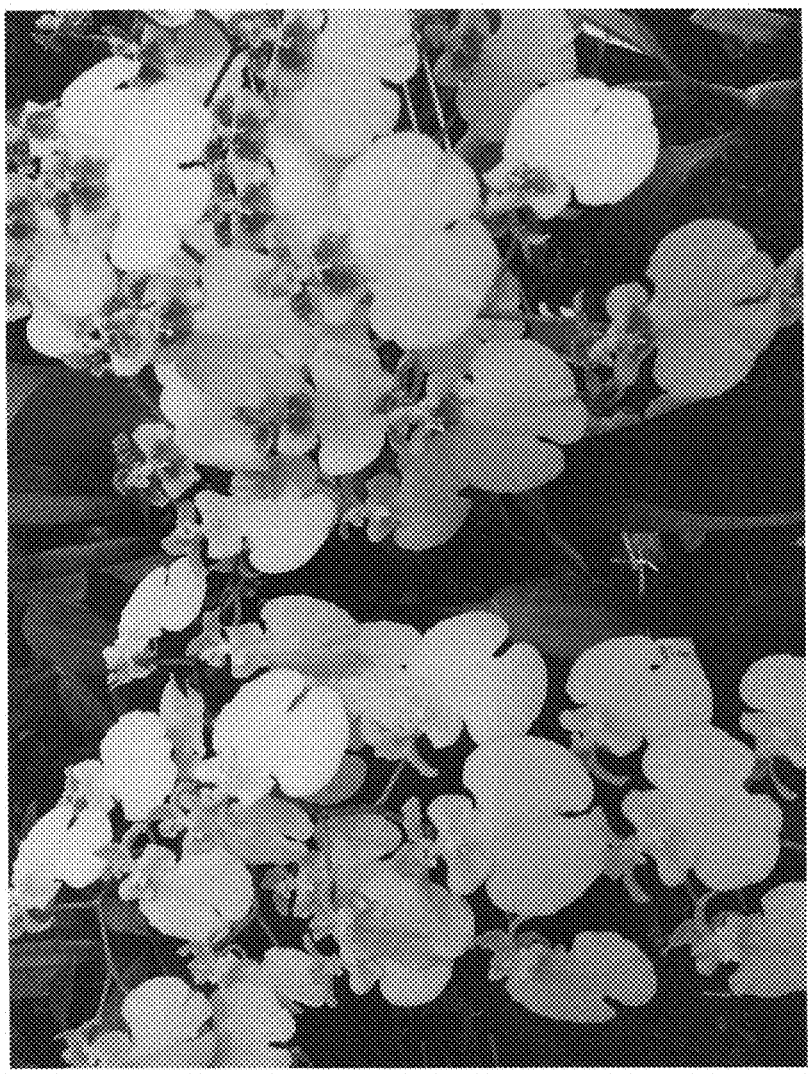

The drawing on the second sheet is a comparison of flowers of *Oncidium* Sweet Sugar 'Lemon Drop' and *Oncidium* Sweet Sugar 'Million Dollar', to illustrate the substantial color difference.

DETAILED BOTANICAL DESCRIPTION

All color references are measured against the Pantone® Color System. Colors and numerical measurements are approximate, as plant growth and development depend on environmental conditions and cultural practices such as: light levels, temperature, water quality, fertilization formula and rate, among others, without however, any variance in genotype.

Plants used for this description are 16 months old in vivo and grown in 3.25 inch square, black plastic pots, grown in a poly-film covered greenhouse in Mountain View, Hi. Day temperatures range from 75-85° F. and night temperatures range from 55-65° F. Light levels are approximately 2500 foot candles. This information reflects the annual variations for the area.

Botanical classification: *Oncidium* Sweet Sugar 'Lemon Drop'.

Parentage: Seedling selected from the cross of the following.

*Seed parent*.—An unnamed cultivar of *Oncidium* Aloha Iwanaga.

*Pollen parent*.—An unnamed cultivar of *Oncidium varicosum*.

The designations above list the Genus and grex for both parents.

Propagation:

*Type*.—Asexual propagation by aseptic tissue culture through Axillary shoot.

*Time to initiate and elongate roots in-vivo*.—Approximately 90 days.

*Time to produce fully rooted young plant*.—Approximately 250 days.

Root description: Velamen covered roots, approximately 0.2 cm in diameter, and white in color with yellow/green growing tip. The exact shades of white and yellow/green vary greatly with minimal changes to environmental conditions.

Plant description: Under optimal growing conditions, plants of the new cultivar attain a mature size of about 28 cm (top of leaf plane) and 5 cm wide (width of largest psuedobulb).

Foliage description:

*Arrangement*.—Sympodial growth habit.

*Quantity of leaves per growth*.—Each sympodial growth has shown four leaves, two on the apex of the psuedobulb and two from the axis at the base.

*Leaf length*.—Leaves measure up to 20 cm in length.

*Leaf width*.—The width of the largest leaf measures 5 cm.

*Leaf shape*.—The shape is lanceolate acuminate from base to tip, texture and substance is slightly undulate and somewhat coriaceous throughout.

*Leaf apex* (*observed*).—The apex measures approximately 22-28 cm.

*Psuedobulb shape*.—The psuedobulb shape is a laterally compressed ovoid.

*Psuedobulb length*.—The psuedobulb is approximately 8-11 cm long.

*Psuedobulb width*.—The psuedobulb is approximately 5 cm wide and 2.8 cm thick.

*Foliage color*.—Under the described growing conditions, the foliage color on both sides of the leaves is similar to Pantone® 7735 (green). There is no vein color distinction. The psuedobulb color is similar to Pantone® 370C (green).

Flower/inflorescence description:

*Description*.—Upright or arching raceme similar in color to Pantone® 7735 (green) approximately 0.3-0.5 cm in diameter, coriaceous, branching, approx. 60 cm long on a first bloom plant with 35 flowers. Each internode is coriaceous in texture, carrying 4-7 flowers spaced 4-6 cm apart and varying between 8-18 cm in length. Buds are ovoid, 0.2-0.4 cm in diameter and 0.3-0.5 cm in length. Bud coloration is unique to each individual flower, being overlaid with different patterns of matte green and matte yellow in a pattern unique to each bud during maturation. As such, selecting an individual color from a color chart would be both difficult and misleading. Pedicels are coriaceous in texture, approximately 0.1 cm in diameter and 0.4 cm in length. Flowers begin approximately ⅔ of the way up the raceme and are spaced 1.5-3.0 cm apart. The size of the inflorescence is appropriate to the overall size of the plant and typical pot size of the cultivar.

*Dimensions*.—Flower dimensions are: natural horizontal spread is 4.5 cm; natural vertical spread is 5.4 cm; dorsal sepal width 0.5 cm; dorsal sepal length 1.2 cm; petal width 0.6 cm; petal length 1 cm; lateral sepal width 0.6 cm; lateral sepal length 1 cm; labellum width 4.5 cm; labellum length 4 cm.

*Coloration*.—The dominant flower color that appears on the sepals, petals and labellum is a bright yellow, Pantone® 106C. The sepals and petals are yellow; Pantone® 106C overlaid with irregular crystalline light green striations similar to Pantone® 379C. The bright yellow extending outward from the callus is Pantone® 108C. The crest of the labellum is a milky white; similar to Pantone® 7499U. The anther cap is bright yellow; Pantone® 106C, faintly overlaid light green; Pantone® 379C at the center. The base color of the column is matte light green; Pantone® 379C, overlaid bright yellow at the base; Pantone® 106C. The pollinia are completely concealed by the anther cap; if this is removed, the pollinia may be extracted. The pollinia are a deeper yellow; Pantone® 108U, but range in shades of yellow as the flower ages.

Quantity of flowers & time to flower:

*Flower longevity*.—Flowers can last longer than 6 weeks on the plant with good environmental conditions. A first bloom plant will produce about 35 flowers depending on environmental conditions.

*Time to flower*.—From fully rooted tissue culture plants is approximately 16 months.

*Natural flowering season*.—This plant has appeared to be free flowering.

*Fragrance*.—No fragrance has been detected.

*Reproductive organs*.—The Stamens, style and stigmas are fused into a short structure called the column, possessing one terminal anther with pollen grains united to a pollinia, which are covered by an anther cap. The stigma is located under the column behind the pollinia. The ovary is inferior, with three carpels being present.

*Column*.—The column is erect with rectangular wings on either side of the stigma, 0.3 cm wide by 0.5 cm long. Coloration is most similar to Pantone® 379C.

*Pollinia*.—Two oval masses of pollen are present, about 0.15 cm in diameter and 0.1 cm long.

*Stigma*.—The stigma is concave, round, very glossy and sticky.

*Ovary*.—The ovary is about 1.1 cm long by 0.2 cm wide.

*Seed*.—Seed production has not been observed.

Disease & pest resistance: Resistance or susceptibility to know pathogens and pests of *Oncidium* have not been observed on plants grown under commercial production conditions.

Hardiness zone: The type plant of *Oncidium* Sweet Sugar 'Lemon Drop' was commercially grown in Mountain View, Hi.—USDA Hardiness Zone 11. Data from other plants of *Oncidium* Sweet Sugar 'Lemon Drop' in other USDA Hardiness zones is currently unavailable.

General observations: Plants of *Oncidium* Sweet Sugar 'Lemon Drop' produce a pleasing arrangement of medium sized, bright yellow, pear shaped flowers with a clean, striking color on a branching raceme that is desirable in proportion for the size of the plant. The flowers are long lasting and pleasantly shaped. The plant grows quickly to sexual maturity.

What is claimed is:

1. A distinct variety of orchid plant named *Oncidium* Sweet Sugar 'Lemon Drop' substantially as illustrated and described herein.

* * * * *